United States Patent
Yang

(10) Patent No.: US 7,933,468 B2
(45) Date of Patent: Apr. 26, 2011

(54) METHOD AND SYSTEM OF MOTION ARTEFACT COMPENSATION IN A SUBJECT

(75) Inventor: Qing Yang, Balwyn North (AU)

(73) Assignee: Apollo Medical Imaging Technology Pty Ltd, North Melbourne, Victoria ( * ) Notice: Subject to any disclaimer, the term of this patent is extended or adjusted under 35 U.S.C. 154(b) by 930 days.

(21) Appl. No.: 11/815,799

(22) PCT Filed: Feb. 16, 2006

(86) PCT No.: PCT/AU2006/000205
§ 371 (c)(1),
(2), (4) Date: Aug. 8, 2007

(87) PCT Pub. No.: WO2006/086845
PCT Pub. Date: Aug. 24, 2006

(65) Prior Publication Data
US 2010/0128941 A1    May 27, 2010

(30) Foreign Application Priority Data
Feb. 16, 2005  (AU) .................................. 2005900727

(51) Int. Cl.
*G06K 9/40*  (2006.01)
*G06K 9/00*  (2006.01)
(52) U.S. Cl. ....................................... 382/274; 382/128
(58) Field of Classification Search .................. 382/274, 382/282, 254, 264, 128
See application file for complete search history.

(56) References Cited

U.S. PATENT DOCUMENTS

| | | | |
|---|---|---|---|
| 6,292,683 B1 | 9/2001 | Gupta et al. | |
| 6,690,965 B1 | 2/2004 | Riaziat et al. | |
| 6,718,055 B1 | 4/2004 | Suri | |
| 7,187,810 B2 * | 3/2007 | Clune et al. | 382/294 |
| 7,783,096 B2 * | 8/2010 | Chen et al. | 382/128 |
| 2003/0191394 A1 | 10/2003 | Simon et al. | |

FOREIGN PATENT DOCUMENTS

| | | |
|---|---|---|
| WO | 02061660 A2 | 8/2002 |
| WO | 2004008969 A1 | 1/2004 |

* cited by examiner

*Primary Examiner* — Yon Couso
(74) *Attorney, Agent, or Firm* — Lumen Patent Firm

(57) ABSTRACT

A method of compensating for motion artefact of a portion of a subject, wherein signal intensity data representing movement of the portion of the subject is recorded and plotted on a display means. The method includes selecting a region of interest (ROI) covering an edge of the moving portion, calculating and plotting data points representing the average signal intensity of the selected ROI at specific time instances, producing a smoothed curve representing the mean of the plotted data points. The method further includes measuring the difference between the plotted data points and the smoothed curve at particular time instances to produce a difference curve, detecting a set of critical points on the difference curve, and interpolating the detected set of critical points to form a curve of equal time intervals for subsequent processing.

35 Claims, 5 Drawing Sheets

METHOD AND SYSTEM OF MOTION ARTEFACT COMPENSATION IN A SUBJECT

FIELD OF THE INVENTION

This invention relates to a method and system of compensating for motion artefacts in a subject, and more particularly relates to a method and system of compensating for motion artefacts in a region of interest of a subject in order to obtain improved data in blood perfusion measurements.

BACKGROUND TO THE INVENTION

The process of measuring blood flow within a body of a subject non-invasively is useful in diagnosing and treating the subject. This is particularly the case where a part of a subject or patient, such as a tissue or organ, suffers from diseases due, for example, to cancer or malfunction. Determining perfusion indices including the blood flow through such a tissue or organ can provide important information to a physician in order to determine an appropriate treatment regime for the patient.

Existing systems pertaining to blood flow information have been disclosed. In general, the systems involve a contrast agent which is delivered as an intravascular bolus during a dynamic imaging session such as computerised tomography (CT), nuclear medicine (NM) or magnetic resonance imaging (MRI). The temporal profile of the image intensity in a pixel or region of interest (ROI) reflects the characteristics of the contrast agent and hence the blood passing through the tissue.

A typical method of obtaining quantitative perfusion indices involves several steps including:

(a) converting the signal intensity profile to the contrast concentration profile depending on the type of imaging modality;

(b) measuring the arterial input function (AIF) from a feeding vessel to the tissue of interest;

(c) measuring the tissue profile;

(d) extracting the tissue impulse residue function (IRF) from the AIF and tissue profile using deconvolution; and (e) calculating quantitative perfusion indices including blood flow, blood volume and mean transit time using the IRF.

However, problems arise when obtaining the above-mentioned perfusion indices when the region of interest includes a tissue or organ that moves over time. Cardiac and respiratory motions are two of the most common sources causing motion artefacts during a dynamic imaging scan. For example when a subject is breathing, the lungs and kidneys and other organs and tissues move involuntarily and create motion artefacts. These motion artefacts make it difficult to obtain data in the region of interest between successive time points at a fixed location within the region of interest due to the movement of the tissue or organ in the region of interest. Taking the example of breathing, a lung could move left or right in the coronal plane, up or down in the coronal plane or even in and out of the coronal plane, for example in the sagittal plane. Due to local tissue stretching and non-uniform distortion, these motion artefacts are not easily correctable using conventional image registration methods for the brain. Breath holding, for up to 20 seconds, is the common method during scanning to minimize respiratory motion artefact, however it is not effective for a typical dynamic scan which takes more than 40 seconds. Other methods of minimizing these motion artefacts are by cardiac and/or respiratory gating during a scan subject to limitations of the hardware used.

The present invention seeks a post-processing method to substantially overcome or at least ameliorate, any one or more of the above-mentioned disadvantages associated with motion artefacts in a region of interest of a subject.

SUMMARY OF INVENTION

According to a first aspect of the invention there is provided a method of compensating for motion artefact of a portion of a subject, wherein signal intensity data representing movement of the portion of the subject is recorded and plotted on a display means, the method comprising the steps of:

selecting a region of interest (ROI) covering an edge of the moving portion to maximise detection of motion artefacts;

calculating and plotting data points representing the average signal intensity of the selected ROI at specific time instances;

smoothing the data points to produce a smoothed curve representing the mean of the plotted data points;

measuring the difference between the plotted data points and the smoothed curve at particular time instances to produce a difference curve;

detecting a set of critical points on the difference curve; and interpolating the detected set of critical points to form a curve of equal time intervals for subsequent processing.

The set of critical points may be local maxima values or local minima values. The local maxima values and the local minima values may respectively represent maxima and minima envelopes of the average signal intensity in the selected ROI. The smoothed curve may be produced using a filter, preferably a curve smoothing filter and more preferably a low pass filter. The subsequent processing may be in relation to obtaining perfusion parameters for perfusion measurements.

According to a second aspect of the invention there is provided computer program means for compensating for motion artefact of a portion of a subject by directing a processor to:

read image data of the subject and plot on a display means signal intensity data of a region of interest (ROI).

enable the user to modify the ROI by covering an edge of the moving portion to maximise detection of motion artefacts;

calculate and plot data points representing the average signal intensity of the selected ROI at specific time instances;

smooth the data points to produce a smoothed curve representing the mean of the plotted data points;

measure the difference between the plotted data points and the smoothed curve at particular time instances to produce a difference curve;

detect a set of critical points on the difference curve; and interpolate the detected set of critical points to form a curve of equal time intervals for subsequent processing.

According to a third aspect of the invention there is provided a system of compensating for motion artefact of a portion of a subject, the system comprising:

scanning means for providing a dynamic image scan of the subject;

processor means linked to the scanning means for retrieving raw image signal intensity data from the scan;

the processor means further;

reading image data of the subject and plotting on a display means signal intensity data of a region of interest (ROI);

enabling selection of a region of interest (ROI) covering an edge of the portion to maximise detection of motion artefacts;

calculating and plotting data points representing the average signal intensity of the selected ROI at specific time instances;

smoothing the data points to produce a smoothed curve representing the mean of the plotted data points;

measuring the difference between the data points and the smoothed curve at particular time instances to produce a difference curve;

detecting a set of critical points on the difference curve; and interpolating the detected set of critical points to form a curve of equal time intervals for subsequent processing.

BRIEF DESCRIPTION OF THE DRAWINGS

The invention will hereinafter be described in a preferred embodiment, by way of example only, with reference to the drawings wherein:

FIG. 1A specifically shows an image at one time point when the organ moves away from the ROI and leaving less organ tissue within the ROI;

FIG. 1B is specifically a scan at another time point when the organ moves towards the ROI and leaving more organ tissue within the ROI;

DETAILED DESCRIPTION OF PREFERRED EMBODIMENT

Figure 1:
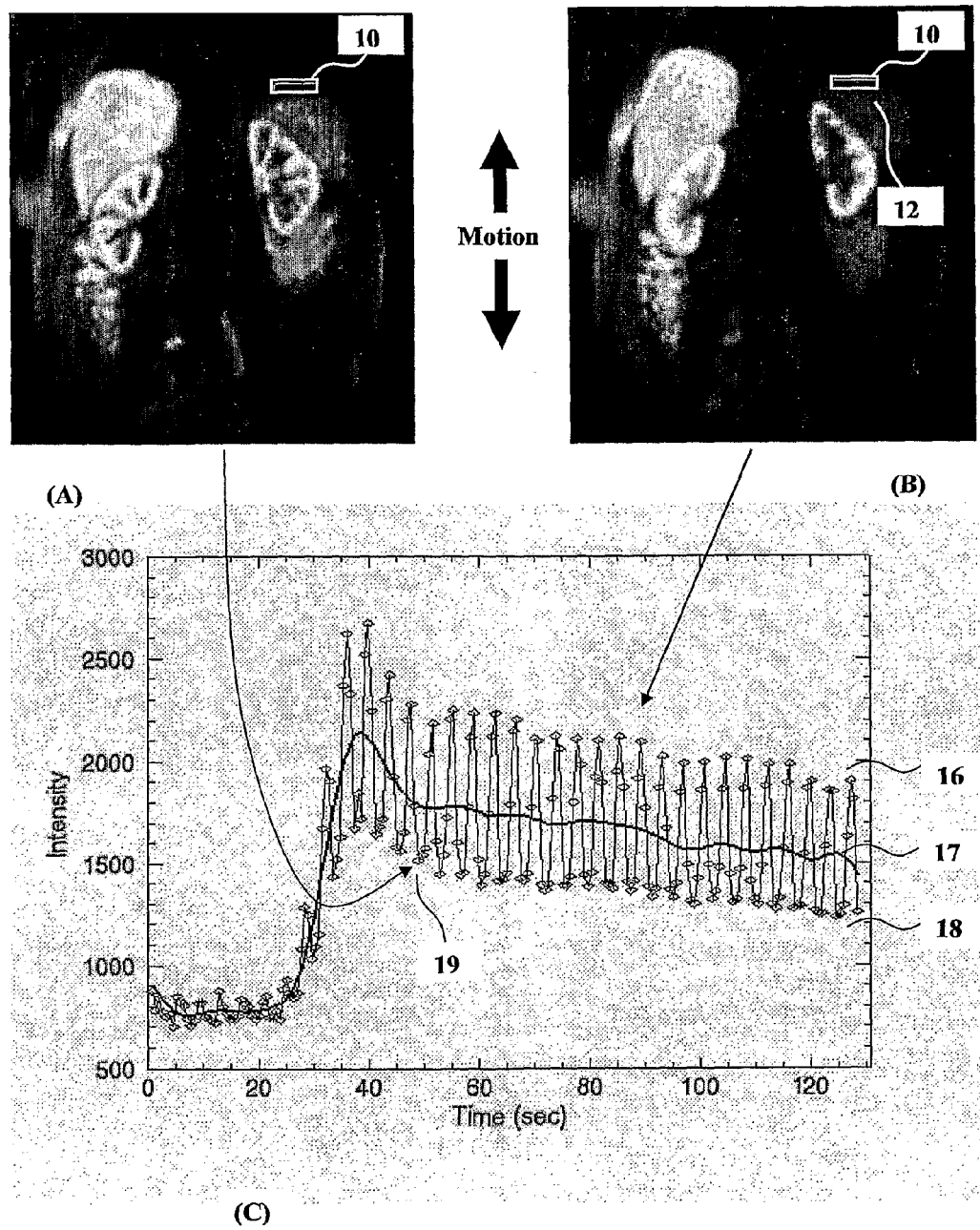
FIGS. 1A and 1B generally shows a contrast enhanced dynamic MRI scan of a patient's abdomen in the coronal plane in which a rectangular region of interest (ROI) is placed over the edge of an abdominal organ to maximize detection of motion artefacts.
FIG. 1C is a plot of an ROI average signal intensity data curve against time with fluctuations representative of the relative displacement of the organ of FIGS. 1A and 1B against time in the coronal plane.

In FIG. 1A there is shown a region of interest 10 over a portion of a subject, in this case an organ from a patient and in particular is located in a coronal plane on the upper edge of the organ 12. As the patient breathes the movement of the organ is mostly in an up and down motion which yields a minimum area of the organ in FIG. 1A which is within the ROI 10 at one time point and a maximum area of the organ in FIG. 1B within the same ROI 10 at another time point.

FIG. 1C shows a plot against time of the fluctuation of average intensity of ROI 10 due to the up and down motion of the organ 12. The minimum signal intensity data points in FIG. 1A and data points representative of when the organ is in a similar position to that shown in FIG. 1A is represented by the low boundary profile 18. The maximum signal intensity data points in FIG. 1B and data points representative of when the organ is in a similar position to that shown in FIG. 1B is shown by the high boundary profile 16. The specific individual data point identified in FIG. 1A is shown at 19 at a time of approximately 51 seconds. Thus with reference to FIGS. 1A and 1C the curve 18 represents the sequence of data points taken at the minimum amount of the organ tissue in the region of interest 10. With reference to FIGS. 1B and 1C the curve 16 represents the sequence of data points taken at the maximum amount of the organ tissue in the region of interest 10. The fluctuation of data points between profiles 16 and 18 essentially shows that the tissue or organ of interest is moving in an up and down fashion due to the breathing of the patient. The reason for the initial delay in recorded values of signal intensity in FIG. 1C is that the contrast injection via a vein may be started at about 10 to 15 seconds, and it takes some time for the contrast to circulate back to the heart and supply to the organ of interests. A smoothed curve Ys(t) 17 is shown between the high and low boundary profiles 16 and 18, and is representative of an average plot between the profiles 16 and 18.

In order to compensate for such motion artefacts a process is performed so as to detect and group data points with similar organ location. Only one group of data points is selected and used for further processing, which is equivalent to the process of gated data acquisition (GDA). For GDA, there is usually an electronic device attached to the patient, so breathing or cardiac activity can be detected in terms of an electric signal presented as a periodic time profile such as ECG. Then the system can use that periodic profile to set a certain threshold to trigger or gate for data acquisition. Typically the group of data points is associated with the maxima values or the minima values respectively.

The first step in the process for compensating for motion artefact is to place a region of interest (ROI) over the edge of the moving organ to maximize detection of motion artefacts by the average ROI signal intensity curve, Y(t). The data points representing the average signal intensity Y(t) of the ROI are then calculated and plotted against time.

Then a curve smoothing low pass filter, such as a boxcar average filter or a moving average filter, is applied to Y(t) to obtain a smoothed curve $Y_s(t)$ 17 as shown in FIG. 1C. The signal intensity fluctuation due to motion artefacts is effectively characterized by the difference curve $$dy = Y - Y_s \quad (1)$$

Figure 2:
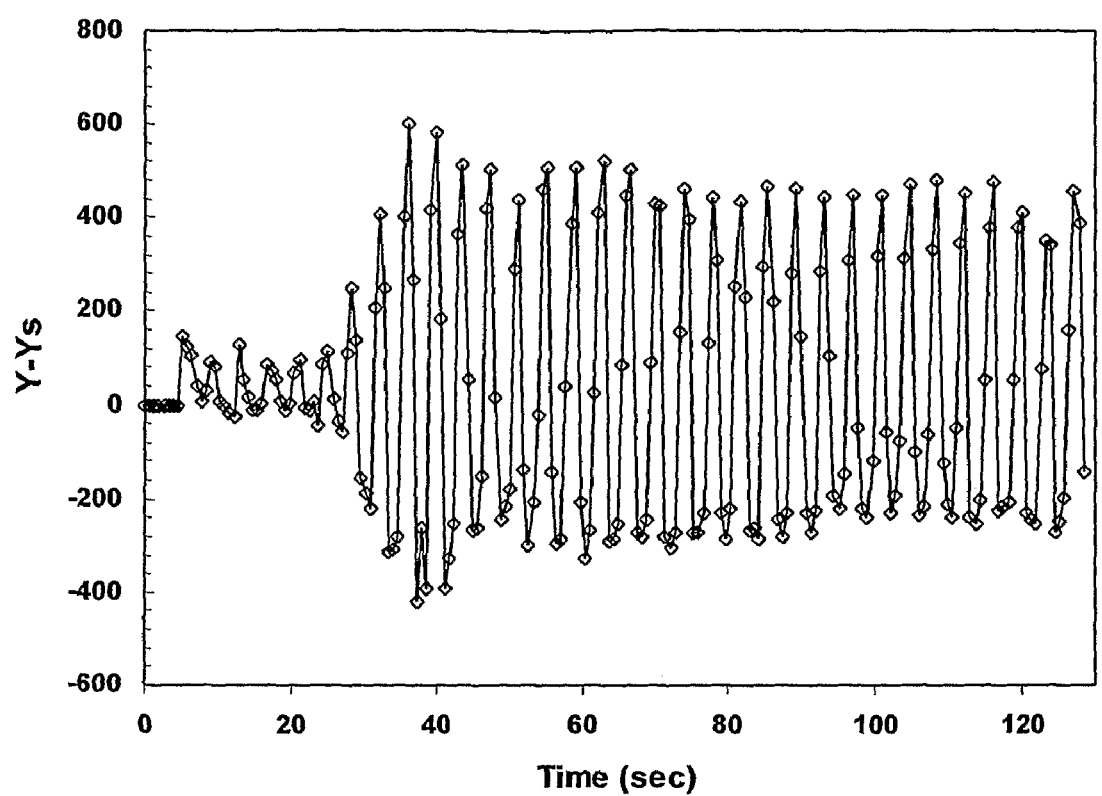
FIG. 2 is a plot of the difference dy between the average ROI signal intensity Y(t) and a smoothed curve Ys(t) against time based on FIG. 1C.

The difference dy between Y(t) and $Y_s(t)$ is calculated since maxima and minima envelopes are not easily detected directly using mathematics, even though each can be visualized from the plot of Y(t) in FIG. 1C. By subtracting the smoothed average profile $Y_s(t)$, the residue dy emphasizes the net fluctuations from the average due to motion artefacts, and this makes detection of local maxima and minima easier mathematically. A plot of dy versus time is shown in FIG. 2.

Figure 3:
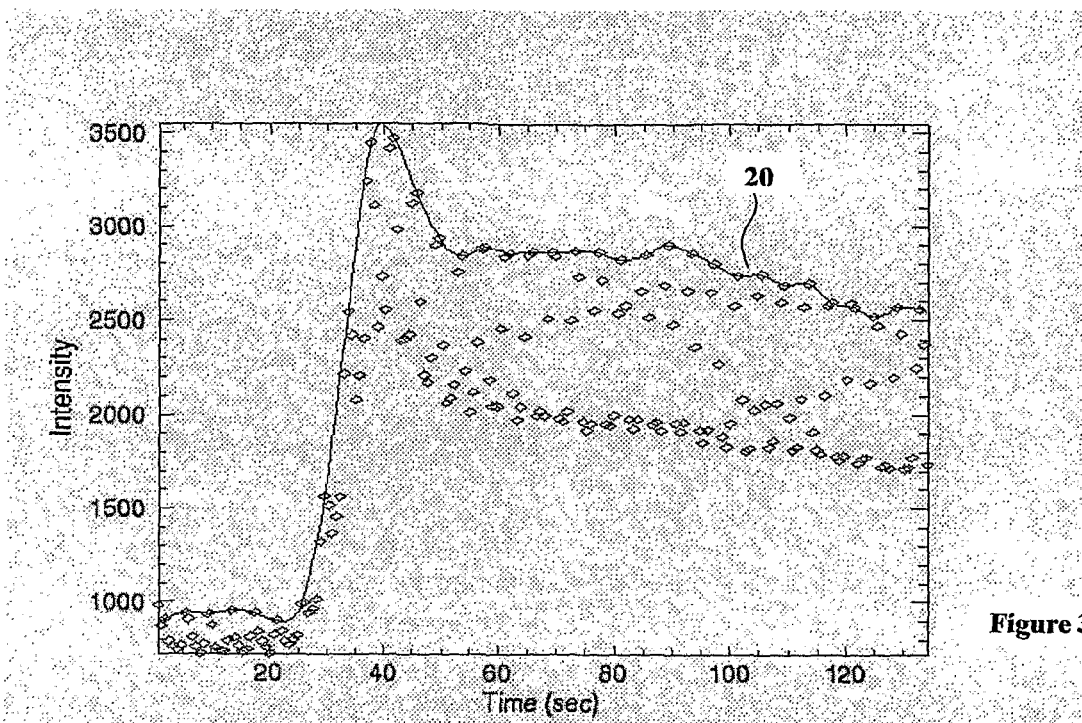
FIG. 3 is a plot showing signal intensity data against time with an interpolated solid line representative of the maxima envelop consisting of the time points when the organ is at a similar position where the organ moves to the uppermost position as shown in FIG. 1B.

To detect the local maxima data points of dy, a moving maximum filter is used with the width of the motion cycle (for example, a breath-in and breath-out cycle, or a cardiac cycle). The width of the motion cycle can be automatically estimated from the fluctuation frequency (between adjacent fluctuating peaks on the curve of FIG. 1C) obtained by performing a fast Fourier transformation of dy. The moving maximum filter identifies each data point being the local maxima within its vicinity of ±width/2. These time points of the detected local dy maxima correspond to the data points on the high boundary profile 16 of Y(t). This group of data points corresponds to those images when the subject is in a similar position, hence with minimized motion artefacts among them. These data points are used to produce an interpolated curve being the maxima envelope 20 as shown in FIG. 3.

Figure 4:
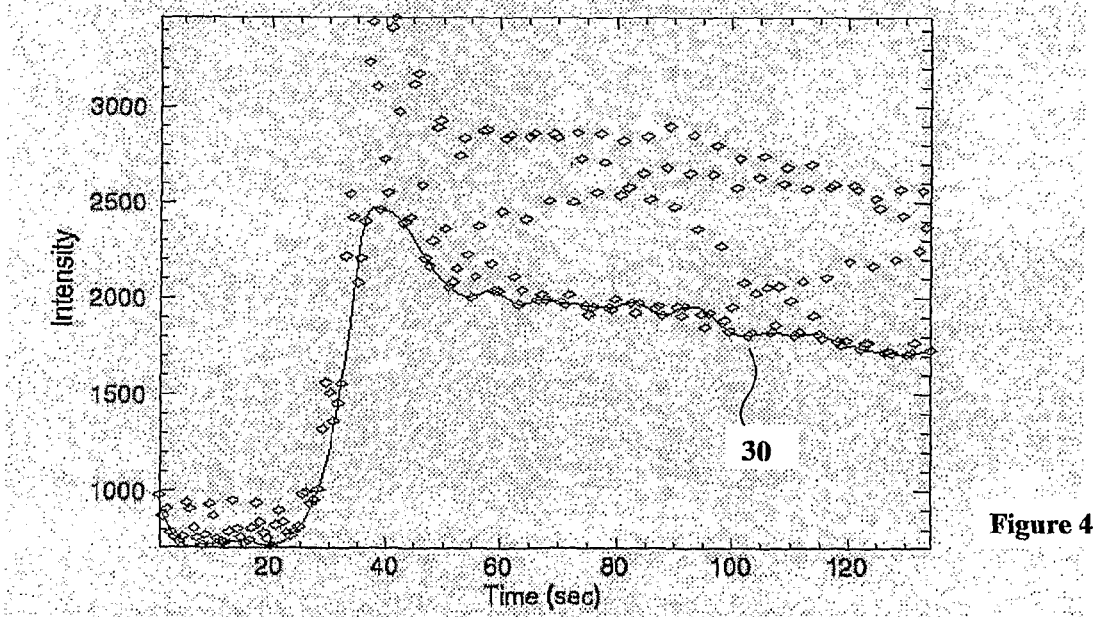
FIG. 4 is a plot of signal intensity data against time with an interpolated solid line representative of the minima envelop consisting of the time points when the organ is at a similar position where the organ moves to the lowermost position as shown in FIG. 1A.

To detect the local minima data points of dy, a moving minimum filter is used with the width of the motion cycle (for example, a breath-in and breath-out cycle, or a cardiac cycle). The width of the motion cycle can be automatically estimated from the fluctuation frequency (between adjacent fluctuating troughs on the curve of FIG. 1C) obtained by performing a fast Fourier transformation of dy. The moving minimum filter identifies each data point being the local minima within its vicinity of ±width/2. These time points of the detected local dy minima correspond to the data points on the low boundary profile 18 of Y(t). This group of data points corresponds to those images when the subject is in a similar position, hence with minimized motion artefacts among them. These data points are used to produce an interpolated curve, being the minima envelope 30 as shown in FIG. 4.

Based on the user's choice, the process derives either the maxima envelope 16 or the minima envelope 18 in order to select a group of data points with minimal motion artefacts among them. Further processing of the dynamic data, for example, the calculations of blood perfusion indices only use the selected group of data points while data values at unselected time points are filled using interpolation. This will minimize motion artefacts on the processing of dynamic data and hence provide more reliable results in regions of interest where tissue or other parts of the subject periodically move.

Figure 5:
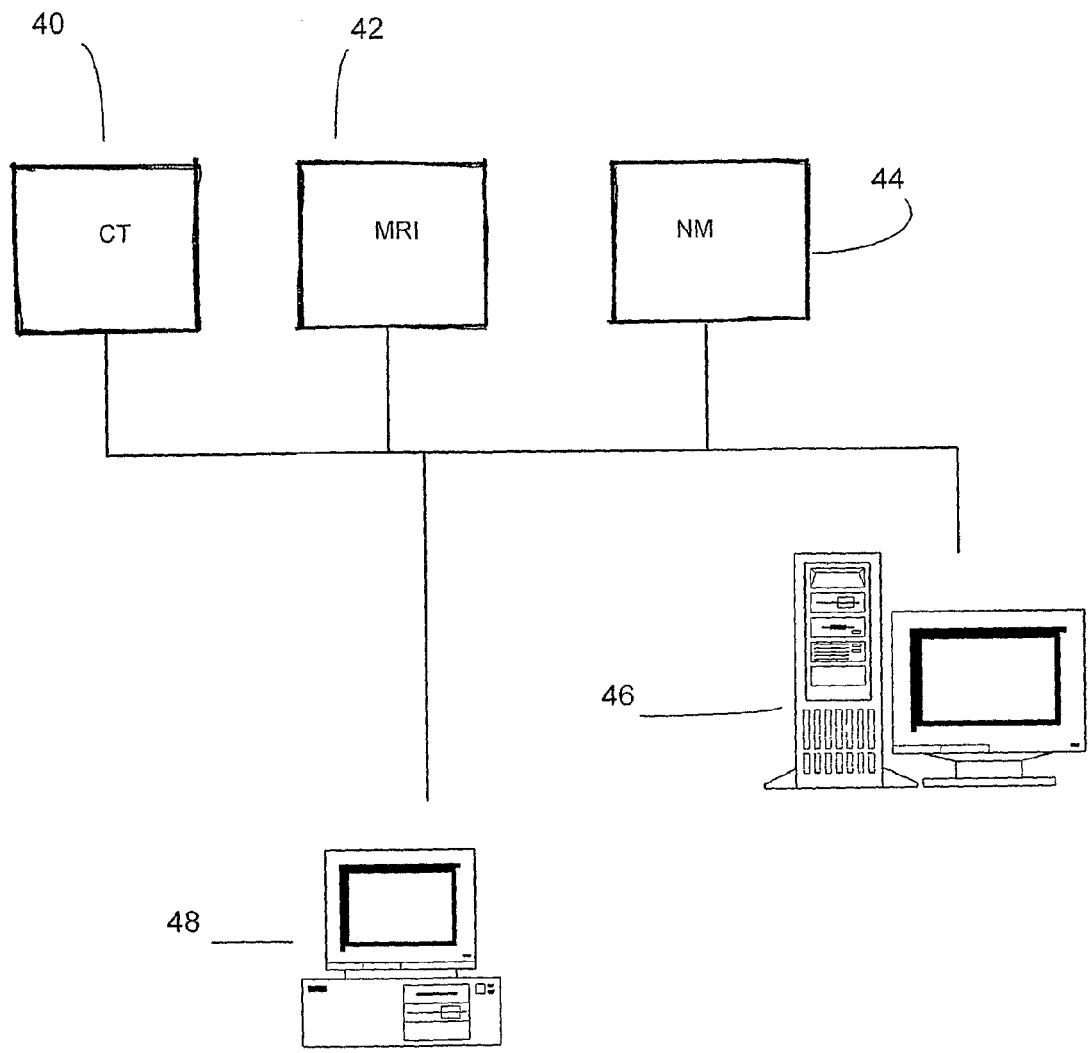
FIG. 5 is a block diagram showing a communications network including a number of scanners linked to a data storage system and a processing system.

With reference to FIG. 5, raw data and/or images collected by a scanner either from a CT scanner 40, MRI scanner 42 or NM scanner 44 are forwarded to a data storage system 46 in the form of a picture archiving communications system (PACS). A computer program operating on processor 48, in the form of a PC, is used to retrieve various images or raw data from any one of the scanners 40, 42 or 44 or from the data storage system 46, and reads the dynamic image data and plots the signal intensities of a region of interest as a function of time. The program processes these images to provide an improved data set for a clinician to use. An example of the data set is as shown in FIGS. 1A, 1B and 1C.

Figure 6:
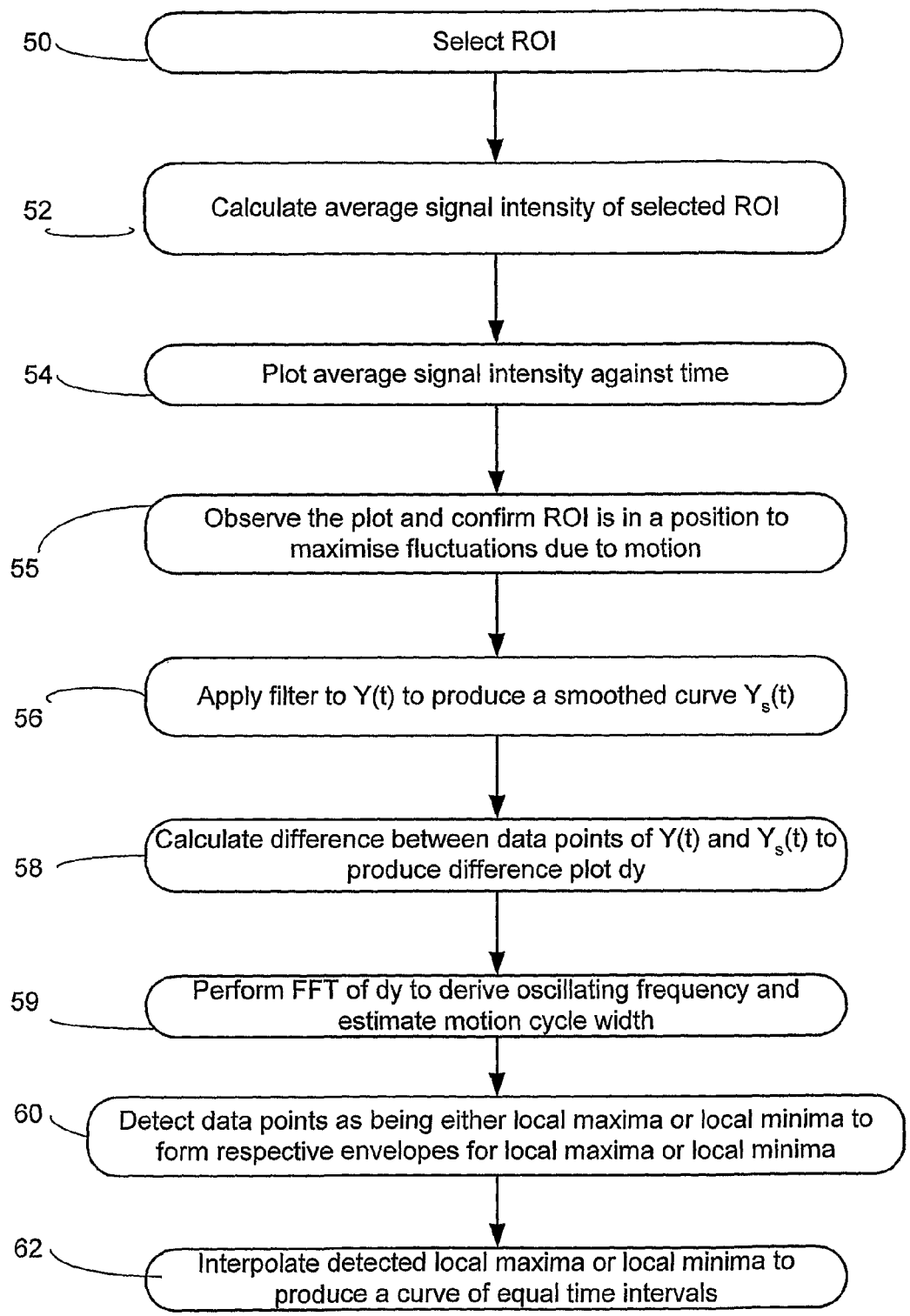
FIG. 6 is a flow diagram showing steps performed by a computer program in order to compensate for motion artefact in a region of interest of a subject in order to obtain improved data in blood perfusion measurements.

Referring to FIG. 6, at step 50 the user selects the ROI which is placed over an edge of the moving portion of the subject. At step 52, the program calculates the average signal intensity of the selected ROI over time and plots these data points versus time at step 54. At step 55, the user observes the plot and confirms that the selected ROI is in a position over the organ edge to maximise fluctuations due to the motion of the organ. At step 56, a low pass filter, incorporated in the computer program, is applied to Y(t) to produce a smoothed curve $Y_s(t)$. At step 58, the program measures the difference dy between the data points Y(t) and $Y_s(t)$ at each time instant to produce a difference plot dy.

At step 59, the program performs a Fast Fourier Transformation of dy to derive the oscillating (fluctuation) frequency and estimate the motion cycle width. The user has the option to further modify this width parameter. At step 60, the program detects the group of data points as either being local maxima or local minima on the difference curve dy, using respectively a moving maximum filter and a moving minimum filter included in the program. These sets of maxima and minima points represent respective maxima and minima envelopes of the average signal intensity against time in the ROI. At step 62, the program then interpolates the detected maxima or minima group of data points to produce a time curve of equal time intervals, known as the maxima envelope or minima envelope respectively, for subsequent processing of perfusion parameters. Such interpolation using the detected group of time points can be applied on a pixel-by-pixel basis for processing of various perfusion maps with minimized motion artefacts.

This embodiment has been described using an example of a dynamic MRI scan of a patient's abdominal organ. The invention is equally applicable to other body organs, not just of humans but animals as well, and using CT or NM scans.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

What is claimed is:

1. A method of compensating for motion artefact of a portion of a subject, wherein signal intensity data representing movement of the portion of the subject is recorded and plotted on a display, the method comprising the steps of:
   selecting on a computer a region of interest (ROI) covering an edge of the moving portion to maximize detection of motion artefacts;
   said computer calculating and plotting data points representing an average signal intensity of the selected ROI at specific time instances;
   said computer smoothing the data points to produce a smoothed curve representing the mean of the plotted data points;
   said computer measuring the difference between the plotted data points and the smoothed curve at particular time instances to produce a difference curve;
   said computer detecting a set of critical points on the difference curve; and
   said computer interpolating the detected set of critical points to form a curve of equal time intervals for subsequent processing.

2. The method according to claim 1, wherein the set of critical points are local maxima.

3. The method according to claim 2, wherein the local maxima represent a maxima envelope of values of the average signal intensity in the selected ROI.

4. The method according to claim 1, wherein the set of critical points are local minima.

5. The method according to claim 4, wherein the local minima represent a minima envelope of values of the average signal intensity in the selected ROI.

6. The method according to claim 1, wherein the step of smoothing uses a curve smoothing filter.

7. The method according to claim 6, wherein the curve smoothing filter is a low pass filter.

8. The method according to claim 3, wherein the step of interpolating produces the maxima envelope.

9. The method according to claim 5, wherein the step of interpolating produces the minima envelope.

10. The method according to claim 1, wherein the smoothed curve is the mean of a high boundary profile and a low boundary profile of the average signal intensity of the selected ROI, the high boundary profile having data points representative of the maximum signal intensity and the low boundary profile having data points representative of the minimum signal intensity.

11. The method according to claim 10, further comprising said computer detecting local maxima on the difference curve using a moving maximum filter and the width of a motion cycle.

12. The method according to claim 10 further comprising said computer detecting local minima on the difference curve using a moving minima filter and the width of a motion cycle.

13. The method according to claim 11, wherein the width of the motion cycle is estimated from a fluctuation frequency of a plot of the difference curve.

14. The method according to claim 13 wherein the fluctuation frequency is obtained by performing a Fast Fourier Transform on the difference curve.

15. The method according to claim 1, wherein the portion of the subject is an organ.

16. The method according to claim 1, wherein the subject is one of a human and an animal.

17. The method according to claim 1, wherein the subsequent processing involves obtaining perfusion parameters for perfusion measurements.

18. A computer program embodied on a computer-readable medium for compensating for motion artefact of a portion of a subject by directing a processor to: read image data of the subject and plot on a display signal intensity data of a region of interest (ROI), enable a user to modify the ROI by covering an edge of the moving portion to maximize detection of motion artefacts; calculate and plot data points representing an average signal intensity of the selected ROI at specific time instances; smooth the data points to produce a smoothed curve representing the mean of the plotted data points; measure the difference between the plotted data points and the smoothed curve at particular time instances to produce a difference curve; detect a set of critical points on the difference curve; and interpolate the detected set of critical points to form a curve of equal time intervals for subsequent processing.

19. A system of compensating for motion artefact of a portion of a subject, the system comprising:
   a scanner for providing a dynamic image scan of the subject;
   a processor linked to the scanner for retrieving raw image signal intensity data from the scan;
   the processor further reading image data of the subject and plotting on a display signal intensity data of a region of interest (ROI);
   enabling selection of a region of interest (ROI) covering an edge of the portion to maximize detection of motion artefacts;
   calculating and plotting data points representing an average signal intensity of the selected ROI at specific time instances;
   smoothing the data points to produce a smoothed curve representing the mean of the plotted data points;
   measuring the difference between the data points and the smoothed curve at particular time instances to produce a difference curve;
   detecting a set of critical points on the difference curve; and
   interpolating the detected set of critical points to form a curve of equal time intervals for subsequent processing.

20. The system according to claim 19, wherein the set of critical points are local maxima.

21. The system according to claim 20, wherein the local maxima represent a maxima envelope of values of the average signal intensity in the selected ROI.

22. The system according to claim 19, wherein the set of critical points are local minima.

23. The system according to claim 22, wherein the local minima represent a minima envelope of values of the average signal intensity in the selected ROI.

24. The system according to claim 19, wherein the processor controls a curve smoothing filter to produce the smoothed curve.

25. The system according to claim 24, wherein the curve smoothing filter is a low pass filter.

26. The system according to claim 21, wherein the interpolating produces the maxima envelope.

27. The system according to claim 23, wherein the step of interpolating produces the minima envelope.

28. The system according to claim 19, wherein the smoothed curve is the mean of a high boundary profile and a low boundary profile of the average signal intensity of the selected ROI, the high boundary profile having data points representative of the maximum signal intensity and the low boundary profile having data points representative of the minimum signal intensity.

29. The system according to claim 28, further comprising a moving maximum filter and the width of a motion cycle to detect local maxima on the difference curve.

30. The system according to claim 28, further comprising a moving minimum filter and the width of a motion cycle to detect local minima on the difference curve.

31. The system according to claim 29, wherein the width of the motion cycle is estimated from the fluctuation frequency of the plot of the difference curve.

32. The system according to claim 31, wherein the fluctuation frequency is obtained by performing a Fast Fourier Transform on the difference curve.

33. The system according to claim 19, wherein the portion of the subject is an organ.

34. The system according to claim 19, wherein the subject is one of a human and an animal.

35. The system according to claim 19, wherein the subsequent processing involves obtaining perfusion parameters for perfusion measurements.

* * * * *